United States Patent [19]

Stanek et al.

[11] Patent Number: 5,354,761
[45] Date of Patent: Oct. 11, 1994

[54] BIPYRIDYLS

[75] Inventors: Jaroslav Stanek, Arlesheim; Giorgio Caravatti, Allschwil; Hans-Georg Capraro, Rheinfelden; Jörg Frei, Hölstein, all of Switzerland

[73] Assignee: Ciba-Geigy Corp., Ardsley, N.Y.

[21] Appl. No.: 69,660

[22] Filed: Jun. 1, 1993

Related U.S. Application Data

[63] Continuation of Ser. No. 819,299, Jan. 9, 1992, abandoned.

[30] Foreign Application Priority Data

Jan. 14, 1991 [CH] Switzerland .................. 85/91-4

[51] Int. Cl.$^5$ .................. C07D 401/04; A61K 31/44
[52] U.S. Cl. .................. 514/334; 514/333; 546/257; 546/193; 540/470; 540/553; 540/450; 540/485; 544/333
[58] Field of Search .................. 546/257; 514/334, 333

[56] References Cited

U.S. PATENT DOCUMENTS

| | | | |
|---|---|---|---|
| 4,086,244 | 4/1978 | Sprague | 549/349 |
| 4,493,726 | 1/1985 | Burdeska et al. | 71/87 |
| 4,598,073 | 7/1986 | Newkome | 514/185 |
| 4,674,229 | 6/1987 | Burdeska et al. | 47/57.6 |
| 4,968,804 | 11/1990 | Stanek et al. | 546/257 |
| 5,064,832 | 11/1991 | Stanek et al. | 514/256 |

FOREIGN PATENT DOCUMENTS

| | | | |
|---|---|---|---|
| 0024779 | 3/1981 | European Pat. Off. | 128/833 |
| 0024780 | 3/1981 | European Pat. Off. | 128/833 |
| 0024781 | 3/1981 | European Pat. Off. | 128/833 |
| 89-5141 | 2/1990 | South Africa | 546/257 |

OTHER PUBLICATIONS

Antonini et al, J. Med. Chem 1981, 24, 1181–1184.
Chem. Abstr. 52, 18415e (1958) Maerker et al.
Chem Abstr 53, 11087d (1959) Smith et al.
Chem Abstr 58, 12460d (1963) Roll et al.
Chem Abstr 98, 97743d (1983) Michael et al.
Maerker et al., J. Am. Chem Soc. 80, 2745–2748 (1958).

*Primary Examiner*—Alan L. Rotman
*Attorney, Agent, or Firm*—Irving M. Fishman; Karen G. Kaiser

[57] ABSTRACT

Compounds of formula I

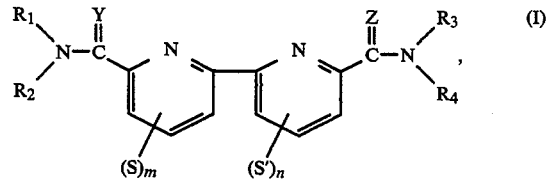

wherein Y, Z, S, S', m, n and $R_1$–$R_4$ are as defined in the description, have valuable pharmaceutical properties and are effective especially against protozoal infections. They are prepared in a manner known per se.

13 Claims, No Drawings

BIPYRIDYLS

This application is a continuation of application Ser. No. 07/819,299, filed Jan. 9, 1992, abandoned The invention relates to compounds of formula I

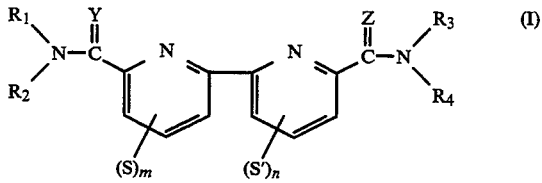

wherein Y is $NR_5$, O or S, Z is $NR_6$, O or S, each of the radicals $R_2$, $R_4$, $R_5$ and $R_6$ independently of the others is hydrogen or lower alkyl, and each of the radicals $R_1$ and $R_3$ independently of the other is hydrogen, lower alkyl, cycloalkyl, aryl-lower alkyl, aryl, free or functionally modified carboxy, hydroxy, etherified or esterified hydroxy, or unsubstituted or mono- or di-substituted amino; wherein the radicals $R_1$ and $R_2$ together may also be lower alkylene, the radicals $R_3$ and $R_4$ together may also be lower alkylene, the radicals $R_2$ and $R_5$ together may also be lower alkylene, and the radicals $R_4$ and $R_6$ together may also be lower alkylene; and wherein each of S and S' independently of the other is a substituent other than hydrogen; m is 0, 1, 2 or 3; and n is 0, 1, 2 or 3, with the proviso that the sum of m and n is at least 1; to tautomers thereof, and to salts thereof, to processes for the preparation of those compounds, to pharmaceutical compositions comprising those compounds, and to the use of those compounds for the therapeutic treatment of the human or animal body or for the preparation of pharmaceutical compositions.

Tautomers can occur, for example, when Y is $NR_5$ and R1 and/or $R_2$ are hydrogen, in which case the corresponding amidine radical, represented in formula I as $—C(=Y)—NR_1R_2$, may, for example, also be in the tautomeric form $—C(—YH)=NR_1$ or $—C(—YH)=NR_2$. A further example: when Z is $NR_6$ and R3 and/or $R_4$ are hydrogen, the corresponding amidine structure, represented in formula I as $—C(=Z)—NR_3R_4$, may also be in the tautomeric form $—C(—ZH)=NR_3$ or $—C(—ZH)=NR_4$. The person skilled in the an is familiar with the occurrence of such and similar tautomers. All these tautomers are covered by the general formula I.

Within the scope of the present Application, the general terms used hereinbefore and hereinafter have preferably the following meanings:

The prefix "lower" denotes a radical having up to and including 7 and especially up to and including 4 carbon atoms.

Alkyl is, for example, $C_1$-$C_{20}$alkyl, and especially lower alkyl.

Lower alkyl is, for example, n-propyl, isopropyl, n-butyl, isobutyl, sec-butyl, tert-butyl, n-pentyl, neopentyl, n-hexyl or n-heptyl, preferably ethyl and especially methyl.

Cycloalkyl contains, for example, from 3 to 8, preferably 5 or 6, ring carbon atoms and is, for example, cyclopropyl, cyclopentyl, cyclohexyl or cycloheptyl.

Aryl-lower alkyl is preferably phenyl-lower alkyl and especially benzyl.

Aryl is, for example, phenyl or naphthyl, such as 1- or 2-naphthyl. The phenyl or naphthyl radicals may be unsubstituted or substituted. Aryl is preferably phenyl that is unsubstituted or substituted by lower alkyl, hydroxy, lower alkoxy, halogen and/or by trifluoromethyl, and is especially unsubstituted phenyl.

Free or functionally modified carboxy is preferably cyano, but may also be, for example, carboxy, esterified carboxy, for example lower alkoxycarbonyl, or amidated carboxy, for example carbamoyl ($—CONH_2$), N-lower alkylcarbamoyl or N,N-di-lower alkylcarbamoyl.

Etherified hydroxy is, for example, alkoxy, such as $C_1$-$C_{20}$alkoxy, and especially lower alkoxy. Esterified hydroxy is, for example, lower alkanoyloxy. Monosubstituted amino is, for example, lower alkylamino. Disubstituted amino is, for example, di-lower alkylamino, $C_4$-$C_6$alkyleneamino, for example piperidino, oxa-$C_3$-$C_5$alkyleneamino, for example morpholino, thia-$C_3$-$C_5$alkyleneamino, for example thiomorpholino, or aza-$C_3$-$C_5$alkyleneamino that is unsubstituted or lower alkyl-substituted at the aza-nitrogen, for example piperazino or 4-lower alkylpiperazino. The terms "oxa-$C_3$-$C_5$", "thia-$C_3$-$C_5$" and "aza-$C_3$-$C_5$" above are to be understood as meaning that the corresponding hetero atom is present in addition to the 3–5 carbon atoms (and not instead of one of the carbon atoms). Disubstituted amino is preferably di-lower alkylamino.

Lower alkylene formed by the groups $R_1$ and $R_2$ or $R_3$ and $R_4$ is preferably $C_2$-$C_7$alkylene and especially $C_4$-$C_5$alkylene, for example 1,4-butylene or 1,5-pentylene.

Lower alkylene formed by the groups $R_2$ and $R_5$ or $R_4$ and $R_6$ is preferably $C_2$-$C_5$alkylene and especially $C_2$-$C_3$alkylene, for example 1,2-ethylene or 1,3-propylene.

Lower alkylenedioxy is, for example, methylenedioxy or ethylenedioxy ($—O—CH_2—CH_2O—$).

Halogen is, for example, fluorine or iodine, especially bromine and more especially chlorine.

Lower alkanoyl is, for example, acetyl, propionyl or pivaloyl, but may also be, for example, formyl.

Examples of a substituent S or S' other than hydrogen are: unsubstituted or substituted hydrocarbon radicals, such as corresponding aliphatic, cycloaliphatic, cycloaliphaticaliphatic, aromatic or araliphatic hydrocarbon radicals, such as alkyl, especially lower alkyl, lower alkenyl, lower alkynyl, or lower alkylene which, as a divalent substituent, is bonded to the ting at two adjacent positions, cycloalkyl, phenyl-lower alkyl, cycloalkyl-lower alkyl or phenyl (substituents of such hydrocarbon radicals are, for example, hydroxy, etherified or esterified hydroxy, such as lower alkoxy, halo-lower alkoxy, lower alkenyloxy, lower alkynyloxy, lower alkylenedioxy or lower alkanoyloxy; halogen, lower alkyl, trifluoromethyl, carboxy and/or functionally modified carboxy, such as esterified carboxy, for example lower alkoxycarbonyl, amidated carboxy, such as carbamoyl, lower alkylcarbamoyl or di-lower alkylcarbamoyl, or cyano); trifluoromethyl; hydroxy; etherified or esterified hydroxy, such as alkoxy, especially lower alkoxy, halo-lower alkoxy, lower alkenyloxy, halo-lower alkenyloxy, lower alkynyloxy, phenyloxy or phenyl-lower alkoxy (the two last-mentioned substituents being unsubstituted or substituted in the phenyl ring, for example by lower alkyl, hydroxy, lower alkoxy, halogen and/or by trifluoromethyl), lower alkylenedioxy which, as a divalent substituent, is bonded to the ring at two adjacent positions, or lower alkanoyloxy; halogen, nitro; amino, substituted amino, such as lower alkylamino, di-lower alkylamino, N-lower alkyl-N-phenyl-lower alkylamino, lower alkyleneamino, oxa-, thia- or aza-lower alkyleneamino (the aza-nitrogen atom being unsubstituted or substituted, preferably by lower alkyl but also, for example, by phenyl, phenyl-lower alkyl or by acyl, for example lower alkanoyl or benzoyl) or acylamino, for example lower alkanoylamino; formyl; acyl, such as lower alkanoyl; carboxy; functionally modified carboxy, such as esterified carboxy, for example lower alkoxycarbonyl, or amidated carboxy, such as carbamoyl, lower alkylcarbamoyl or di-lower alkylcarbamoyl, or cyano; sulfo (—$SO_3H$); functionally modified sulfo, such as sulfamoyl, lower alkylsulfamoyl, di-lower alkylsulfamoyl or phenylsulfamoyl; and etherified mercapto, which may be oxidised, such as lower alkylthio, lower alkylsulfinyl or lower alkylsulfonyl. Preferred substituents S and S' are lower alkyl, lower alkoxy and halogen.

When the symbol m (or n) in a compound of formula I is 2 or 3, the corresponding 2 or 3 substituents S (or S') may be the same or different.

Salts of compounds according to the invention are especially pharmaceutically acceptable, non-toxic salts. For example, compounds of formula I containing basic groups can form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or, for example, with amino acids, such as aspartic acid or glutamic acid. When more basic groups are present than one, mono- or poly-salts can be formed. Compounds of formula I containing an acidic group, for example carboxy, and a basic group, for example amino, may be, for example, in the form of internal salts, i.e. in zwitterionic form, or a part of the molecule may be in the form of an internal salt and another part in the form of a normal salt.

For isolation or purification purposes it is also possible to use pharmaceutically unsuitable salts, for example picrates or perchlorates. Only the pharmaceutically acceptable, nontoxic salts are used therapeutically, and those salts are therefore preferred.

Depending on their structure, the compounds of the present invention may be in the form of isomeric mixtures or pure isomers.

The compounds according to the invention have valuable, especially pharmacologically acceptable, properties. In particular, they have a pronounced, specific inhibitory action on the enzyme S-adenosylmethionine decarboxylase (SAMDC). SAMDC, as a key enzyme, plays an important role in polyamine biosynthesis, which takes place in virtually all mammal cells, including human cells. SAMDC regulates the concentration of polyamines in the cell. Inhibition of the enzyme SAMDC results in a reduction in the polyamine concentration. Since a reduction in the polyamine concentration brings about inhibition of cell growth, it is possible by administering SAMDC-inhibiting substances to inhibit the growth of both eukaryotic and prokaryotic cells and even to kill cells or inhibit the onset of cell differentiation.

Inhibition of the enzyme SAMDC can be demonstrated, for example, by the method of H. G. Williams-Ashmann and A. Schenone, Biochem. Biophys. Res. Communs. 46, 288 (1972). The compounds of the invention have minimum $IC_{50}$ values of approximately 1 µM.

An advantage of the compounds according to the invention is that they inhibit diamine oxidase to a small extent only as compared with their pronounced inhibitory action on SAMDC, and they are well tolerated. According to J. Jaenne and D. R. Morris, Biochem. J. 218, 974 (1984), inhibition of diamine oxidase is disadvantageous since it can lead to the accumulation of putrescine and to indirect SAMDC activation.

The compounds of formula I are therefore useful, for example, for treating benign and malignant tumours. They can bring about the regression of tumours and also prevent the spread of tumour cells and the growth of micrometastases. Moreover, they can be used, for example, for treating protozoal infections, such as, for example trypanosomiasis, malaria, or inflammation of the lungs caused by *Pneumocystis carinii.*

For example, the effectiveness of the compounds of formula I and their salts, referred to as "test compounds" in the following test descriptions, against trypanosomiasis can be demonstrated in vitro by means of the "Long Incubation-Low Inoculation" test (LLIT) and the $^3H$-hypoxanthine incorporation test.

The LLIT is used to determine a minimal inhibitory concentration and a maximal tolerable concentration of the test compounds when acting against trypanosomes (bloodstream forms of Trypanosoma brucei rhodesiense, a human-pathogenic agent of African sleeping sickness) over a relatively long period (long-term incubation). For that purpose, trypanosomes are incubated on a microtitre plate with various concentrations of the relevant test compound. The incubation conditions are as follows: Bloodstream forms of Trypanosoma brucei rhodesiense are cultured axenically at 37° C. and 5% $CO_2$ in a medium having the following composition: 9.75 g of MEM powder ("Minimum Essential Medium"; Gibco, USA; see also Eagle, H., Science 130, 432 (1959)), 6 g of HEPES (N-2-hydroxyethylpiperazine-N'-2-ethanesulfonic acid, Calbiochem GmbH, Federal Republic of Germany), 1 g of glucose, 2.2 g of $NaHCO_3$, 10 ml of MEM NEAA (non-essential amino acid solution), dissolved in distilled water ad 1000 ml and adjusted to pH 7.4 with 4N NaOH, 15% heat-inactivated horse serum (inactivation 30 minutes at 56° C.), Baltz component (0.1 mM hypoxanthine, 0.016 mM thymidine, 2 mM sodium pyruvate and 0.2 mM mercaptoethanol), and 10 µg of gentamycin per ml of medium, in the presence or absence of various concentrations of the test compounds. After an exposure time of 4 days, the test is evaluated visually and the MIC and the MTC are determined. MIC denotes the "Minimal Inhibitory Concentration", i.e. the lowest concentration of test compound at which cells having normal morphology or motility are no longer present. MTC denotes the "Maximal Tolerable Concentration", i.e. the highest concentration of test compound at which, in comparison with a control without test compound, at least 80% of the trypanosomes still survive. A typical MIC of the test compounds of formula I, their tautomers or their salts is near 0.5 µM or more, and a typical MTC near 0.1 µM or more.

The $^3H$-hypoxanthine incorporation test is used to determine the sensitivity of trypanosomes to a compound on short-term incubation. The principle of the incorporation test is based on the incubation of the trypanosomes with the radioactively labelled purine base $^3H$-hypoxanthine. The trypanosomes are unable to synthesise this base themselves and are therefore dependent on an external source. Incorporation of the purine base is proportional to the growth and the metabolic activity of the trypanosomes. As in the LLIT, the trypanosomes are incubated on a microtitre plate with decreasing concentrations of the relevant test compound. Pre-incubation is for a period of 24 hours, and incubation with the purine base a further 16 hours (total duration 40 hours). The cells are harvested, washed and transferred to a filter paper, scintillation liquid is added, and the cells are measured in a β-counter. The control (batch without test compound of formula I) is set as 100% incorporation of the purine base, or metabolic activity, and the remaining batches containing test compound of formula I are given as a percentage of the control. An $IC_{50}$ is defined as the concentration at which the incorporation/metabolic activity values of the batches containing test compound are reduced by 50% as compared with the control (Lit.: Brun, R., et al., Acta Tropica 46, 361–368 (1989)). A typical $IC_{50}$ value of the test compounds of formula I, their tautomers or their salts is near 0.25 μM or more.

The compounds of formula I can be used as selective SAMDC-inhibitors either on their own or in combination with other pharmacologically active substances. Combination with, for example, (a) inhibitors of other enzymes of polyamine biosynthesis, for example ornithine decarboxylase inhibitors, (b) inhibitors of protein kinase C, (c) inhibitors of tyrosine protein kinase, (d) cytokines, (e) negative growth regulators, (f) aromatase inhibitors, (g) anti-oestrogens or (h) conventional cytostatic active ingredients, is possible.

Preferred are compounds of formula I wherein Y is NH, O or S, Z is NH, O or S, each of the radicals $R_2$ and $R_4$ independently of the other is hydrogen or lower alkyl, and each of the radicals $R_1$ and $R_3$ independently of the other is hydrogen, lower alkyl, $C_3$–$C_8$cycloalkyl, phenyl-lower alkyl, phenyl, carboxy, hydroxy or amino; wherein the radicals $R_1$ and $R_2$ together may also be $C_2$–$C_7$alkylene and the radicals $R_3$ and $R_4$ together may also be $C_2$–$C_7$alkylene; and wherein each of S and S′ independently of the other is $C_1$–$C_{20}$alkyl, $C_3$–$C_8$cycloalkyl, phenyl-lower alkyl, $C_3$–$C_8$cycloalkyl-lower alkyl, phenyl, $C_1$–$C_{20}$alkoxy, phenyl-lower alkoxy, phenyloxy, halogen or lower alkylthio; m is 0 or 1; and n is 0 or 1; with the proviso that the sum of m and n is at least 1; phenyl groups in the above definitions being unsubstituted or substituted by lower alkyl, hydroxy, lower alkoxy, halogen and/or by trifluoromethyl; tautomers thereof, and salts thereof.

Especially preferred are compounds of formula I wherein Y is NH, O or S, Z is NH, O or S, each of the radicals $R_2$ and $R_4$ independently of the other is hydrogen or lower alkyl, and each of the radicals $R_1$ and $R_3$ independently of the other is hydrogen, lower alkyl, $C_3$–$C_8$cycloalkyl, phenyl-lower alkyl, phenyl, carboxy, hydroxy or amino; wherein the radicals $R_1$ and $R_2$ together may also be $C_2$–$C_7$alkylene and the radicals $R_3$ and $R_4$ together may also be $C_2$–$C_7$alkylene; and wherein each of S and S′ independently of the other is lower alkyl, phenyl-lower alkyl, lower alkoxy, halogen or lower alkylthio; m is 0 or 1; and n is 0 or 1; with the proviso that the sum of m and n is at least 1; tautomers thereof, and salts thereof.

More especially preferred are compounds of formula I wherein Y is NH, O or S, Z is NH, O or S, the radicals $R_2$ and $R_4$ are each hydrogen or lower alkyl, the radicals $R_1$ and $R_3$ are each hydrogen, lower alkyl, $C_5$–$C_6$cycloalkyl or hydroxy, S and S′ are each lower alkyl, lower alkoxy or halogen, and m and n are each 1; tautomers thereof, and pharmaceutically acceptable salts thereof.

Most especially preferred are compounds of formula I wherein Y is NH, Z is NH, the radicals $R_2$ and $R_4$ are each hydrogen, the radicals $R_1$ and $R_3$ are each hydrogen, lower alkyl, $C_5$–$C_6$cycloalkyl or hydroxy, S and S′ are attached at the 4- and 4′-positions, respectively, and are each lower alkyl, lower alkoxy or halogen, and m and n are each 1, tautomers thereof, and pharmaceutically acceptable salts thereof.

As sub-groups of a group of compounds of formula I, attention is drawn to: (a) compounds of formula I wherein the groups

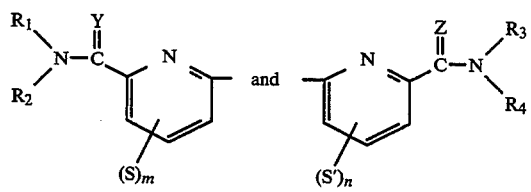

are identical; (b) compounds of formula I wherein $R_1$, $R_2$, $R_3$ and $R_4$ are each hydrogen; (c) compounds of formula I wherein the substituents S and S′ are attached at the 4-position (or 4′-position); and (d) compounds of formula I wherein Y and Z are each NH.

The invention relates especially to the specific compounds described in the Examples, and pharmaceutically acceptable salts thereof.

The compounds of formula I can be prepared in a manner known per se, for example as follows: in a compound of formula II

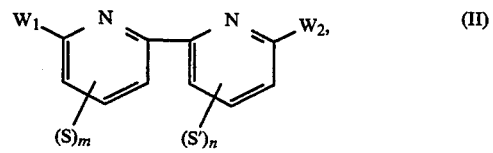

wherein $W_1$ and $W_2$ are radicals that can be converted into the groups —C(=Y)NR$_1$R$_2$ and —C(=Z)NR$_3$R$_4$, respectively, converting the radicals $W_1$ and $W_2$ into the groups —C(=Y)NR$_1$R$_2$ and —C(=Z)NR$_3$R$_4$, respectively; the symbols Y, Z, $R_1$–$R_4$, S, S′, m and n being as defined under formula I; and, if desired, converting a resulting compound of formula I into a different compound of formula I, and/or converting a resulting salt into the free compound or into a different salt, and/or converting a resulting free compound of formula I having salt-forming properties into a salt.

In the following, more detailed description of the process, the symbols Y, Z, $R_1$–$R_6$, S, S′, m and n are each as defined under formula I unless indicated otherwise.

In the intermediates of formula II, $W_1$ and $W_2$ are, for example, free or functionally modified carboxy, especially halocarbonyl, carbamoyl, N-lower alkylcarbamoyl, cyano, an imino-lower alkyl ester [—C(=N-H)—OAlk (Alk=lower alkyl)] or an imino-lower alkylthiol ester [—C(=NH)—SAlk].

In the preparation of (mono- or di-)amidines of formula I (Y=NR$_5$ and/or Z=NR$_6$), the groups $W_1$ and/or $W_2$ in a compound of formula II may be, for example: an imino-lower alkyl ester (=imino-lower alkyl ether) or imino-lower alkylthiol ester or in each case an acid addition salt thereof, for example —C(=N-H)—OC$_2$H$_5$ or —C(=NH)—SC$_2$H$_5$, or —C(=N-

H)—OC$_2$H$_5$.HCl or —C(=NH)—SC$_2$H$_5$.HI; cyano or N-lower alkylcarbamoyl.

Reaction of (mono- or di-)imino-lower alkyl esters or (mono- or di-)imino-lower alkylthiol esters of formula II (in the form of acid addition salts) with ammonia or primary or secondary amines yields the unsubstituted or mono- or di-substituted (mono- or di-)amidines of formula I.

By analogy, it is possible to react the (mono- or di-)imino-lower alkyl esters or (mono- or di-)imino-lower alkylthiol esters of formula II in free form, these preferably being prepared in situ, with an ammonium salt, for example $^{\oplus}NH_4Cl^{\ominus}$, or with an ammonium salt of a primary or secondary amine, to give the unsubstituted or mono- or di-substituted (mono- or di-)amidines of formula I.

(Mono- or di-)cyano compounds of formula II can be convened into unsubstituted or mono- or di-substituted (mono- or di-)amidines of formula I, for example by reaction with an alkali metal amide, for example KNH$_2$, or by reaction with a primary or secondary (di-)lower alkylammonium halide, for example $^{\oplus}NH_3CH_3$ Cl$^{\ominus}$, or with a salt of hydroxylamine, for example $^{\oplus}NH_3OH$ Cl$^{\ominus}$.

(Mono- or di-)N-hydroxyamidines of formula I can be converted into (mono- or di-)amidines of formula I by reduction, for example catalytic hydrogenation, for example with H$_2$/Raney nickel [cf. DE-OS 2 705 609 or J. Med. Chem. 15, 182–186 (1972)].

Compounds of formula II wherein W$_1$ and/or W$_2$ are N-lower alkylcarbamoyl can be converted, for example by reaction with POCl$_3$ or PCl$_5$, into the corresponding imido acid chlorides [—C(=NH—Alk)—Cl] which, after reaction with ammonia or with a primary or secondary amine, yield substituted (mono- or di-)amidines of formula I[cf. Chem. Abstr. 81, 91185a (1974)].

Compounds of formula I wherein the radicals R$_2$ and R$_5$ together and/or the radicals R$_4$ and R$_6$ together are lower alkylene can be prepared, for example, by reacting a compound of formula II wherein W$_1$ and/or W$_2$ are cyano with an α, ω-diamino-lower alkane, for example 1,2-diaminoethane, preferably in the presence of catalytic amounts of carbon disulfide.

In the preparation of (mono- or di-)carbamoyl compounds of formula I (Y=O and/or Z=O), the groups W$_1$ and/or W$_2$ in a compound of formula II may be, for example: carboxy, halocarbonyl (e.g. —COCl), lower alkoxycarbonyl or cyano. The formation of unsubstituted or mono- or di-substituted (mono- or di-)carbamoyl compounds of formula I from corresponding intermediates of formula II wherein W$_1$ and/or W$_2$ are carboxy, halocarbonyl or lower alkoxycarbonyl, by reaction with ammonia or with primary or secondary amines, is known per se. Intermediates of formula II wherein W$_1$ and/or W$_2$ are cyano can be converted into unsubstituted or mono- or di-substituted (mono- or di-)carbamoyl compounds of formula I, for example by partial hydrolysis, according to a Graf-Ritter reaction, or via imino-lower alkyl ester salts. The conditions for the hydrolysis of the cyano intermediates can be selected such that the reaction is stopped at the amide stage. Hydrolysis by means of acids is especially suitable for that purpose, there coming into consideration, for example, 80% sulfuric acid (with heating), polyphosphoric acid (at 110°–150° C.), hydrobromic acid/glacial acetic acid (room temperature, formic acid or without solvent), hydrogen chloride in ethereal solution followed by the addition of water or aqueous hydrochloric acid, or boron halides.

By means of the Graf-Ritter reaction it is also possible to prepare N-substituted amides from (mono- or di-)nitriles of formula II. To that end the (mono- or di-)nitriles are reacted in the presence of a strong acid, especially 85–90% sulfuric acid, or polyphosphoric acid, formic acid, boron trifluoride or other Lewis acids, but not aluminium chloride, with compounds that are able to form carbonium ions in the acidic medium, that is to say, for example, with olefins, such as propylene, or with alcohols, such as ethanol.

The (mono- or di-)imino-lower alkyl esters (in the form of acid addition salts) are obtained, for example, by the acid-catalysed addition of alcohols to the (mono- or di-)nitriles of formula II. The addition may also be catalysed by means of bases, for example alcoholates, such as sodium methoxide, in which case the (mono- or di-)imino-lower alkyl esters are obtained in free form.

The (mono- or di-)amides are obtained from the (mono- or di-)imino-lower alkyl esters by means of a Pinner cleavage by thermal decomposition of the imino ester salts at temperatures above approximately 80° C.

On the other hand, the (mono- or di-)imino-lower alkyl esters may also be prepared, for example, from (mono- or di-)carbamoyl compounds of formula II by reaction with tri-lower alkyloxonium tetrafluoroborate, especially $^{\oplus}O(C_2H_5)_3$ BF$_4^{\ominus}$ ("Meerwein salt").

The (mono- or di-)imino-lower alkylthiol esters are prepared, for example, by S-alkylation of the corresponding (mono- or di-)thiocarbamoyl compounds (see below); for the alkylation there may be used, for example, lower alkyl halides or lower alkyl tosylates or, again, the "Meerwein salt" mentioned above.

In the preparation of (mono- or di-)thiocarbamoyl compounds of formula I (Y=S and/or Z=S), the groups W$_1$ and/or W$_2$ in a compound of formula II may be, for example: carbamoyl, lower alkyl- or di-lower alkyl-carbamoyl (in these cases the compound of formula II corresponds to a compound of formula I), cyano or halocarbonyl. The formation of unsubstituted or mono- or di-substituted (mono- or di-)thiocarbamoyl compounds of formula I by reacting corresponding intermediates of formula II, wherein W$_1$ and/or W$_2$ are, for example, as defined above, with agents that introduce sulfur is known per se [cf., for example, Chem. Reviews 61, 45–86 (1961)]. Intermediates of formula II wherein W$_1$ and/or W$_2$ are carbamoyl, lower alkyl- or di-lower alkyl-carbamoyl can be converted into unsubstituted or mono- or di-substituted (mono- or di-)thiocarbamoyl compounds of formula I, for example by reaction with phosphorus pentasulfide (P$_4$S$_{10}$) or aluminium trisulfide (Al$_2$S$_3$) or, especially, with Lawesson's reagent [2,4-bis-(4-methoxyphenyl)-2,4-dithioxo-1,3,2,4-dithiadiphosphetane].

Intermediates of formula II wherein W$_1$ and/or W$_2$ are cyano can be converted into (mono- or di-)thiocarbamoyl compounds of formula I, for example by reaction with ammonia and hydrogen sulfide in ethanol [see, for example, Il Farmaco 41, 346–354 (1986)] or with hydrogen sulfide in pyridine and triethylamine [see Example 3], and those wherein W$_1$ and/or W$_2$ are halocarbonyl,for example, by reaction with phosphorus pentachloride, hydrogen sulfide and ammonia.

Compounds of formula II wherein W$_1$ and W$_2$ are carboxy are prepared, for example, by oxidising a compound of formula III

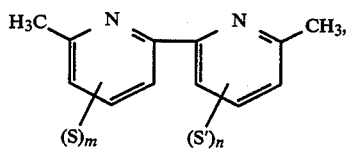

for example with KMnO$_4$ or K$_2$Cr$_2$O$_7$. It is a condition of this reaction that the substituents S and S' must not be sensitive to oxidation—that is to say they may not be lower alkyl, for example—or they must be protected against oxidation by means of protecting groups.

Furthermore, from compounds of formula III it is also possible to prepare, for example, compounds of formula II wherein W$_1$ and W$_2$ are cyano, by nitrosating the compounds of formula III, for example, analogously to Chem. Pharm. Bull. 25, 1821 (1977) [=C.A. 88, 121089 m (1978)] with ethyl nitrite in the presence of alkali metal amides in liquid ammonia to form the corresponding dialdoximes, and heating the latter together with POCl$_3$.

Compounds of formula II wherein W$_1$ and W$_2$ are cyano are preferably prepared by oxidising a compound of formula VI

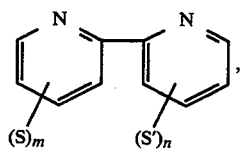

for example with meta-chloroperbenzoic acid or H$_2$O$_2$ [see, for example, Bull. Chem. Soc. Japan 52, 1408 (1979)], to form a di-N-oxide, dimethylating the di-N-oxide, for example with dimethyl sulfate, and reacting the resulting N,N'-dimethoxy derivative with, for example, sodium cyanide. Instead of dimethylating the mentioned di-N-oxide and reacting it with, for example, NaCN, it is also possible, for example, to react it directly with trimethylsilyl cyanide (cf. Synthesis 1984, 681 ) or diethyl cyanophosphonate [cf. Il Farmaco 41, 346–354 (1986)].

Compounds of formula II wherein W$_1$ and W$_2$ are cyano are also prepared, for example, by reacting a compound of formula IV

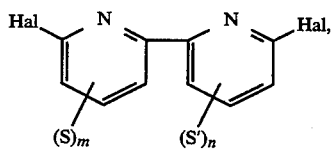

wherein Hal is halogen, with cyanating agents, for example sodium cyanide or potassium cyanide—optionally with catalysis by means of Pd[P(C$_6$H$_5$)$_3$]$_4$ or phase transfer catalysis, for example with 18-crown-6 ether-or copper(I) cyanide, especially in pyridine or dimethylformamide [cf. Chem. Rev. 87, 779 (1987)].

On the other hand, the halogen groups in a compound of formula IV may, for example, alternatively be converted into trimethylammonium halide radicals by reaction with trimethylamine. The trimethylammonium halide radicals can then be converted into cyano groups, for example by treatment with sodium cyanide in an aqueous medium, compounds of formula II wherein W$_1$ and W$_2$ are cyano again being obtained.

Furthermore, compounds of formula II wherein W$_1$ and W$_2$ are carboxy can be prepared from compounds of formula IV by dimetallisation of the compounds of formula IV and then reaction with, for example, CO$_2$. The metallisation can be carried out using, for example, lithium-introducing agents, for example n-butyl lithium, in which case di-(Li) intermediates are formed. If the metallisation is carried out using lithium-introducing agents and copper(I) salts, then di-(lithium cuprates), for example di-(CuLi) compounds, are obtained as intermediates. Furthermore, the metallisation may be carried out using, for example, magnesium, in which case dimagnesium halides, di-(MgHal) compounds, are obtained as intermediates.

Compounds of formula II wherein W$_1$ and W$_2$ are cyano can also be prepared, for example, by twice diazotising a compound of formula V

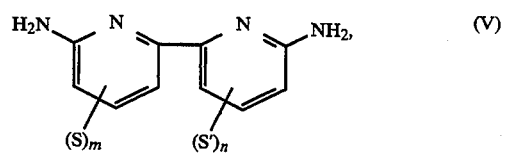

for example using sodium nitrite, and then reacting with, for example, copper(I) cyanide (Sandmeyer reaction).

Compounds of formula II wherein W$_1$ and W$_2$ are cyano, and compounds of formulae III, IV and VI, are prepared, for example, by reacting a compound of formula VIIa

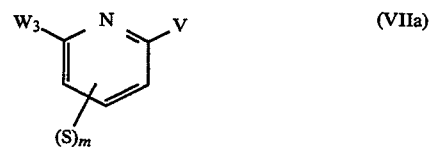

with a compound of formula VIIb

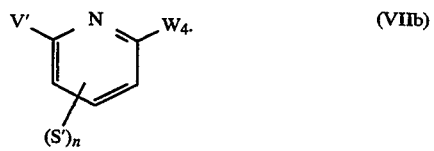

In the compounds of formulae VIIa and VIIb, W$_3$ is cyano and W$_4$ is methyl, halogen or hydrogen, and V and V' are functional groups that are suitable for linking (hetero)aryls to bi(hetero)aryls. Examples of suitable groups V and V' are (a) magnesium halide -MgHal and Hal (Hal=halogen), (b) lithium —Li and Hal, or (c) lithium cuprates, for example with the radical —CuLi, and Hal.

Mention may also be made of (d) the coupling of two (identical or different) lithium derivatives (V=V'=Li) in the presence of, for example, CuCl$_2$/O$_2$ or [CuI.P(n-C$_4$H$_9$)$_3$]$_4$/O$_2$ [cf. J. Organomet. Chem. 56, 53 (1973)].

A further linking possibility is (e) the coupling of a compound of formula VIIa wherein V=Li to a (N-heterocyclic) compound of formula VIIb wherein V'=H, cf. Chem. Ber 113, 2739 (1980).

Compounds of formula V can be prepared, for example, by reduction of the corresponding dinitro compounds, for example by hydrogenation or using Sn(II)Cl$_2$. Furthermore, compounds of formula V can also be prepared, for example, from the corresponding compounds of formula IV by reacting the latter with an alkali metal amide, for example sodium or potassium amide.

Free compounds of formula I having salt-forming properties obtainable according to the process can be convened into their salts in a manner known per se, compounds having basic properties by treatment with acids or suitable derivatives thereof, and compounds having acidic properties by treatment with bases or suitable derivatives thereof.

Because of the close relationship between the compounds of formula I in the free form and in the form of thier salts, the references made throughout this text to the free compounds or their salts is to be understood as including the corresponding salts or free compounds, as appropriate and expedient.

The compounds, including their salts, may also be obtained in the form of hydrates, or their crystals may include, for example, the solvent used for crystallisation.

Mixtures of isomers obtainable according to the invention can be separated into the individual isomers in a manner known per se, racemates, for example, by the formation of salts with optically pure salt-forming reagents and separation of the diastereoisomeric mixture so obtainable, for example by means of fractional crystallisation.

The above-mentioned reactions can be carded out under reaction conditions that are known per se, in the absence or, customarily, in the presence of solvents or diluents, preferably solvents or diluents that are inert towards the reagents used and dissolve them, for example in alcohols, such as methanol or ethanol, nitriles, such as acetonitrile, halogenated hydrocarbons, such as methylene chloride, water or mixtures of those solvents, in the absence or presence of catalysts, condensing agents or neutralising agents, depending on the nature of the reaction and/or of the reactants at reduced, normal or elevated temperature, for example at room temperature or in a temperature range of from approximately $-70°$ C. to approximately $190°$ C., preferably from approximately $-20°$ C. to approximately $150°$ C., for example at the boiling point of the solvent used, under atmospheric pressure or in a closed vessel, optionally under pressure, and/or in an inert atmosphere, for example under a nitrogen atmosphere.

In the process of the present invention there are preferably used those starting materials which result in the compounds described at the beginning as being especially valuable.

The invention relates also to those forms of the process in which a compound obtainable as intermediate at any stage of the process is used as starting material and the remaining process steps are carded out, or in which a starting material is formed under the reaction conditions or is used in the form of a derivative, for example a salt.

The present invention relates also to pharmaceutical compositions that comprise one of the pharmacologically active compounds of formula I as active ingredient. Compositions for enteral, especially oral, and parenteral administration are especially preferred. The compositions comprise the active ingredient on its own or, preferably, together with a pharmaceutically acceptable carder. The dose of active ingredient depends on the disease to be treated, and on the species, its age, weight and individual condition, and on the mode of administration.

The pharmaceutical compositions comprise from approximately 5% to approximately 95% active ingredient, dosage forms that are in single dose form preferably comprising from approximately 20% to approximately 90% active ingredient, and dosage forms that are not in single dose form preferably comprising from approximately 5% to approximately 20% active ingredient. Unit dose forms, such as dragées, tablets or capsules, comprise from approximately 0.05 g to approximately 1.0 g of active ingredient.

The pharmaceutical compositions of the present invention are prepared in a manner known per se, for example by means of conventional mixing, granulating, confectioning, dissolving or lyophilising processes. For example, pharmaceutical compositions for oral administration can be obtained by combining the active ingredient with one or more solid carders, optionally granulating a resulting mixture, and processing the mixture or granules, if desired, by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches and also carboxymethyl starch, cross-linked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric coatings, there being used inter alia concentrated sugar solutions, which may comprise gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Pharmaceutical compositions for oral administration are also dry-filled hard gelatin capsules, and soft sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and, where appropriate, stabilisers. In soft capsules the active ingredient is preferably dissolved or suspended in suitable liquid excipients, such as fatty oils, paraffin oil or liquid polyethylene glycols, it likewise being possible to add stabilisers.

Other oral dosage forms are, for example, syrups prepared in customary manner which comprise the active ingredient, for example, in suspended form and in a concentration of approximately from 5% to 20%, preferably approximately 10% or in a similar concentration that provides a suitable single dose when administered, for example, in an amount of 5 or 10 ml. Also suitable are, for example, powdered or liquid concentrates for the preparation of shakes, for example in milk. Such concentrates may also be packed in single dose quantities.

Suitable pharmaceutical compositions for rectal administration are, for example, suppositories that consist of a combination of the active ingredient with a suppository base. Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that comprise viscosity-increasing substances, for example sodium carboxymethylcellulose, sorbitol and/or dextran, and, if desired, stabilisers. The active ingredient, without or together with excipients, can also be in the form of a lyophilisate and be made into a solution prior to parenteral administration by the addition of suitable solvents.

The solutions used, for example, for parenteral administration can also be used as infusion solutions.

The invention relates also to a method of treating the pathological conditions mentioned above. The compounds of the present invention can be administered prophylactically or therapeutically, for example for the treatment of tumours that are responsive to inhibition of S-adenosylmethionine decarboxylase, or for the treatment of protozoal infections in mammals, for example humans, that require the mentioned treatment on account of such a disorder, the compounds of the present invention preferably being administered in the form of pharmaceutical compositions. For a body weight of approximately 70 kg, a daily dose of from approximately 0.1 g to approximately 10 g, preferably from approximately 0.5 g to approximately 5 g, of a compound of the present invention is administered.

The following Examples illustrate the present invention; temperatures are given in degrees Celsius.

EXAMPLE 1

6,6'-Diamidino-4,4'-dimethyl-2,2'-bipyridine dihydrochloride 0.023 g (0.001 g-atom) of sodium are dissolved under nitrogen in 15 ml of absolute methanol. 2.34 g (0.01 mol) of 6,6'-dicyano-4,4'-dimethyl-2,2'-bipyridine are added to that solution, and the resulting mixture is stirred at room temperature for 2 days. 1.34 g (0.025 mol) of ammonium chloride, 10 ml of absolute methanol and 20 ml of a saturated ethanolic ammonia solution are then added, and the mixture is stirred at 70° for one hour. After cooling, the reaction mixture is concentrated to dryness by evaporation and the residue is crystallised from dilute hydrochloric acid, yielding the title compound, m.p.>240°; MS(FAB): (M+H)+=269; $^1$H-NMR (D$_2$O): $\delta$=8.39 (d,2H); 7.88 (d,2H) 2.46 (s,6H).

The starting material is prepared as follows, according to a1), a2) or a3):

(a) 6,67-Dicyano-4,4'-dimethyl-2,2'-bipyridine a1) 12.96 g (0.06 mol) of 4,4'-dimethyl-2,2'-bipyridine di-N-oxide are added at 75° to 14.25 ml (0.15 mol) of dimethyl sulfate, and the mixture is kept at 80° for 15 minutes. The reaction mixture is then cooled, dissolved in 30 ml of water and slowly added dropwise to an ice-cooled solution of 17.4 g (0.33 mol) of sodium cyanide in 66 ml of water. The mixture is then stirred in an ice-bath for one hour. The resulting precipitated material is filtered off with suction, washed with water and dried, yielding starting material (a), m.p. 251°–253°.

a2) 5.3 g (0.033 mol) of diethyl cyanophosphonate are added dropwise to a solution of 2.16 g (0.01 mol) of 4,4'-dimethyl-2,2'-bipyridine di-N-oxide in 20 ml of acetonitrile and 2.23 g (0.022 mol) of triethylamine, and the mixture is boiled under reflux for 16 hours. The reaction mixture is concentrated by evaporation and water is added to the residue. The insoluble material is filtered off with suction, washed with water, dried and recrystallised from ethanol, yielding starting material (a), m.p. 251°–253°.

a3) 10 ml (0.08 mol) of trimethylsilyl cyanide are added to a solution of 2.16 g (0.01 mol) of 4,4'-dimethyl-2,2'-bipyridine di-N-oxide in 10 ml of acetonitrile and 5.6 ml (0.04 mol) of triethylamine, and the mixture is boiled under reflux for 24 hours. After cooling, the reaction mixture is diluted with 100 ml of methylene chloride, washed with dilute sodium hydrogen carbonate solution and water, dried over sodium sulfate, filtered and concentrated by evaporation. The residue is crystallised from methanol and corresponds to starting material (a), m.p. 251°–253°, IR (CH$_2$Cl$_2$): 2240 cm$^{-1}$ (C$\equiv$N); $^1$H-NMR (CDCl$_3$): $\delta$=8.52 (d,2H); 7.58 (d,2H); 2.53 (s,6H).

EXAMPLE 2

6,6'-Diamidino-5,5'-dimethyl-2,2'-bipyridine dihydrochloride 4.3 g (0.021 mol) of triethyloxonium tetrafluoroborate are added under nitrogen to a solution of 3.02 g (0.01 mol) of 5,5'-dimethyl-6,6'-dithiocarbamoyl-2,2'-bipyridine (see Example 3) in 50 ml of methylene chloride. After 2 hours, 0.98 g (0.007 mol) of potassium carbonate and 0.9 ml of water are added to the reaction solution, which is then stirred for a short time and filtered, and the filtrate is washed with ice-water. The organic phase is dried over sodium sulfate and concentrated by evaporation. The crude bis-thioimino ether, 1.8 g (0.005 mol), is dissolved in 20 ml of absolute ethanol, 0.64 g (0.012 tool) of ammonium chloride is added, and the mixture is boiled under reflux for 12 hours. After cooling, the mixture is filtered, a small amount of ethanolic hydrochloric acid is added to the filtrate, and the mixture is then concentrated by evaporation. The residue is purified by chromatography on Amberlite®XAD 1180 (water as eluant), yielding the title compound.

EXAMPLE 3

5,5'-Dimethyl-6,6'-dithiocarbamoyl-2,2'-bipyridine

A stream of dry hydrogen sulfide is introduced for a period of 7 hours at 40° into a solution of 2.34 g (0.01 mol) of 6,6'-dicyano-5,5'-dimethyl-2,2'-bipyridine in 30 ml of pyridine and 3.0 ml (0.02 mol) of triethylamine. The reaction mixture is stirred for a further 15 hours at 40°, cooled and poured into water. The mixture is extracted with methylene chloride, and the organic solution is dried over sodium sulfate and concentrated to dryness by evaporation, yielding the title compound.

The starting material is prepared as follows:

(a) 6,6'-Dicyano-5,5'-dimethyl-2,2'-bipyridine 12.96 g (0.06 mol) of 5,5'-dimethyl-2,2'-bipyridine di-N-oxide are added at 75° to 14.25 ml (0.15 mol) of dimethyl sulfate, and the mixture is kept at 80° for 15 minutes. The reaction mixture is then cooled, dissolved in 30 ml of water and slowly added dropwise to an ice-cooled solution of 17.4 g (0.33 mol) of sodium cyanide in 66 ml of water. The mixture is then stirred for one hour in an ice-bath. The resulting material is filtered off with suction, washed with water and dried, yielding the title compound.

EXAMPLE 4

6,6'-Dicarbamoyl-4,4'-dimethyl-2,2'-bipyridine 0.47 g (0.002 mol) of 6,6'-dicyano-4,4'-dimethyl-2,2'-bipyridine are suspended in 8 ml of ethanol and 8 ml of 1N sodium hydroxide solution, and the mixture is boiled under reflux for 2 hours. After cooling, the reaction mixture is concentrated by evaporation and the residue is taken up in 10 ml of water. The insoluble material is filtered off with suction, washed with a small amount of water, dried and recrystallised from dilute ethanol, yielding the title compound.

EXAMPLE 5

6,6'-Bis-N-hydroxyamidino-4,4'-dimethyl-2,2'-bipyridine

A mixture of 0.47 g (0.002 mol) of 6,6'-dicyano-4,4'-dimethyl-2,2'-bipyridine, 0.6 g 0.0056 mol) of sodium carbonate and 0.7 g (0.01 mol) of hydroxylamine hydrochloride in 20 ml of water and 10 ml of ethanol is boiled under reflux for 2 hours. After cooling, the resulting material is filtered off with suction and recrystallised from water, yielding the title compound, m.p. 272°-276°.

EXAMPLE b 6

The following compounds are prepared analogously to Examples 1 to 3:
a) 6,6'-diamidino-4,4'-dichloro-2,2'-bipyridine,
b) 6,6'-diamidino-4,4'-dimethoxy-2,2'-bipyridine,
c) 6,6'-diamidino-3,3'-dimethyl-2,2'-bipyridine,
d) 6,6'-dithiocarbamoyl-4,4'-dimethyl-2,2'-bipyridine,
e) 6,6'-bis-N-methylamidino-4,4'-dimethyl-2,2'-bipyridine,
f) 6,6'-bis-N,N-dimethylamidino-4,4'-dimethyl-2,2'-bipyridine,
g) 6,6'-bis- 1-piperidinoiminomethyl-4,4'-dimethyl-2,2'-bipyridine,
h) 6,6'-bis-1-pyrrolidinoiminomethyl-4,4'-dimethyl-2,2'-bipyridine, and
i) 6,6'-bis-N-cyclopentylamidino-4,4'-dimethyl-2,2'-bipyridine.

EXAMPLE 7

Capsules containing 0.25 g of active ingredient, for example one of the compounds according to Examples 1 to 6i, can be prepared as follows:

| Composition (for 5000 capsules) | |
|---|---|
| active ingredient | 1250 g |
| talc | 180 g |
| wheat starch | 120 g |
| magnesium stearate | 80 g |
| lactose | 20 g |

The powdered substances are pressed through a sieve having a mesh size of 0.6 mm and mixed. 0.33 g portions of the mixture are introduced into gelatin capsules by means of a capsule-filling machine.

What is claimed is:

1. A compound of formula I

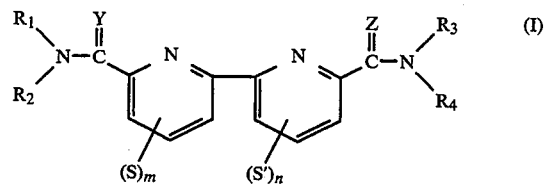

wherein Y is $NR_5$, O or S, Z is $NR_6$, O or S, each of the radicals $R_2$, $R_4$, $R_5$ and $R_6$ independently of the others is hydrogen or lower alkyl, and each of the radicals $R_1$ and $R_3$ independently of the other is hydrogen, lower alkyl, $C_3-C_8$cycloalkyl, aryl-lower alkyl wherein aryl is unsubstituted naphthyl or is phenyl that is unsubstituted or substituted by one or more substituents selected form the group comprising lower alkyl, hydroxy, lower alkoxy, halogen and trifluoromethyl, aryl as defined above, cyano, carboxy, lower alkoxycarbonyl, carbamoyl, N-lower alkylcarbamoyl, N,N-di-lower alkylcarbamoyl, hydroxy, $C_1-C_{20}$alkoxy, lower alkanoyloxy, amino, lower alkylamino, di-lower alkylamino, $C_4-C_6$alkyleneamino, oxa-$C_3-C_5$alkyleneamino, thia-$C_3-C_5$alkyleneamino or aza-$C_3-C_5$alkyleneamino that is unsubstituted or lower alkyl-substituted at the aza-nitrogen and wherein each of S and S' independently of the other is an unsubstituted hydrocarbon radical selected from $C_1-C_{20}$alkyl, lower alkenyl, lower alkynyl, $C_3-C_8$cycloalkyl, phenyl-lower alkyl, $C_3-C_8$cycloalkyl and phenyl or one of these hydrocarbon radicals that is substituted by hydroxy, lower alkoxy, halo-lower alkoxy, lower alkenyloxy, lower alkynyloxy, lower alkylenedioxy, lower alkanoyloxy, halogen, lower alkyl, trifluoromethyl, carboxy, lower alkoxycarbonyl, carbamoyl, lower alkylcarbamoyl, di-lower alkylcarbamoyl or cyano; trifluorormethyl; hydroxy; lower alkoxy; halo-lower alkoxy; lower alkenyloxy; halo-lower alkenyloxy; lower alkynyloxy; phenyloxy or phenyl-lower alkoxy wherein phenyl is unsubstituted or substituted by one or more substitutents selected from the group comprising lower alkyl, hydroxy, lower alkoxy, halogen and trifluorormethyl; lower alkanoyloxy; halogen; nitro; amino; lower alkylamino; di-lower alkylamino; N-lower alkyl-N-phenyl-lower alkylamino, lower alkyleneamino, oxa-, thia- or aza-lower alkyleneamino or (N-lower alkyl-aza)-, (N-phenyl-aza)-, (N-phenyl-lower alkyl-aza)-, (N-lower alkanoyl-aza)- or (N-benzoyl-aza)-lower alkyleneamino; lower alkanoyl; carboxy; lower alkoxycarbonyl; carbamoyl; lower alkylcarbamoyl; di-lower alkylcarbamoyl; cyano; sulfo; sulfamoyl; lower alkylsulfamoyl; di-lower alkylsulfamoyl; phenylsulfamoyl; lower alkythio; lower alkylsulfinyl; and lower alkylsulfonyl; m is 0, 1, 2 or 3; and n is 0, 1, 2 or 3, with the proviso that the sum of m and n is at least 1; tautomers thereof, or a pharmaceutically acceptable salt thereof.

2. A compound of formula I according to claim 1 wherein Y is NH, O or S, Z is NH, O or S, each of the radicals $R_2$ and $R_4$ independently of the other is hydrogen or lower alkyl, and each of the radicals $R_1$ and $R_3$ independently of the other is hydrogen, lower alkyl, $C_3-C_8$cycloalkyl, phenyl-lower alkyl, phenyl, carboxy, hydroxy or amino; and wherein each of S and S' independently of the other is $C_1$–$C_{20}$alkyl, $C_3$–$C_8$cycloalkyl, phenyl-lower alkyl, $C_3$–$C_8$cycloalkyl-lower alkyl, phenyl, $C_1$–$C_{20}$alkoxy, phenyl-lower alkoxy, phenyloxy, halogen or lower alkylthio; m is 0 or 1; and n is 0 or 1; with the proviso that the sum of m and n is at least 1; phenyl groups in the above definitions being unsubstituted or substituted by lower alkyl, hydroxy, lower alkoxy, halogen and/or by trifluoromethyl; tautomers thereof, or a pharmaceutically acceptable salt thereof.

3. A compound of formula I according to claim 1 wherein Y is NH, O or S, Z is NH, O or S, each of the radicals $R_2$ and $R_4$ independently of the other is hydrogen or lower alkyl, and each of the radicals $R_1$ and $R_3$ independently of the other is hydrogen, lower alkyl, $C_3$–$C_8$cycloalkyl, phenyl-lower alkyl, phenyl, carboxy, hydroxy or amino; and wherein each of S and S' independently of the other is lower alkyl, phenyl-lower alkyl, lower alkoxy, halogen or lower alkylthio; m is 0 or 1; and n is 0 or 1; with the proviso that the sum of m and n is at least 1; tautomers thereof, or a pharmaceutically acceptable salt thereof.

4. A compound of formula I according to claim 1 wherein Y is NH, O or S, Z is NH, O or S, the radicals $R_2$ and $R_4$ are each hydrogen or lower alkyl, the radicals $R_1$ and $R_3$ are each hydrogen, lower alkyl, $C_5$–$C_6$cycloalkyl or hydroxy, S and S' are each lower alkyl, lower alkoxy or halogen, and m and n are each 1; tautomers thereof, or a pharmaceutically acceptable salt thereof.

5. A compound of formula I according to claim 1 wherein Y is NH, Z is NH, the radicals $R_2$ and $R_4$ are each hydrogen, the radicals $R_1$ and $R_3$ are each hydrogen, lower alkyl, $C_5$–$C_6$cycloalkyl or hydroxy, S and S' are attached at the 4- and 4'-positions, respectively, and are each lower alkyl, lower alkoxy or halogen, and m and n are each 1, tautomers thereof, or a pharmaceutically acceptable salt thereof.

6. A compound of formula I according to claim 1 wherein Y is NH, Z is NH, the radicals $R_2$ and $R_4$ are each hydrogen, $R_1$ and $R_3$ are each hydrogen, S and S' are attached at the 4- and 4'-positions, respectively, and are each lower alkyl, lower alkoxy or halogen, and m and n are each 1, tautomers thereof, or a pharmaceutically acceptable salt thereof.

7. 6,6'-Diamidino-4,4'-dimethyl-2,2'-bipyridine according to claim 1 or a pharmaceutically acceptable salt thereof.

8. 6,640-Diamidino-5,5'-dimethyl-2,2'-bipyridine according to claim 1 or a pharmaceutically acceptable salt thereof.

9. 6,6'-Diamidino-4,4'-dimethoxy-2,2'-bipyridine according to claim 1 or a pharmaceutically acceptable salt thereof.

10. 6,6'-Diamidino-3,3'-dimethyl-2,2'-bipyridine according to claim 1 or a pharmaceutically acceptable salt thereof.

11. 6,6'-Bis-N-hydroxyamidino-4,4'-dimethyl-2,2'-bipyridine according to claim 1 or a pharmaceutically acceptable salt thereof.

12. A pharmaceutical composition for the treatment of a disorder selected from the group comprising trypanosomiasis, malaria or inflammation of the lung caused by *Pneumocystis carinii*, comprising a dose of a compound of formula I, a tautomer thereof, or a pharmaceutically acceptable salt thereof according to claim 1 that is effective against a disorder selected from the group comprising trypanosomiasis, malaria or inflammation of the lung caused by *Pneumocystis carinii*, together with at least one pharmaceutically acceptable career.

13. A method of treating a mammal suffering from a disorder selected from the group comprising trypanosomiasis, malaria or inflammation of the lung caused by *Pneumocystis carinii*, which comprises administering a dose of a compound of formula I, a tautomer thereof, or a pharmaceutically acceptable salt thereof according to claim 1 that is therapeutically effective against the disorder selected from the group comprising trypanosomiasis, malaria or inflammation of the lung caused by *Pneumocystis carinii*, to a mammal in need of such treatment.

* * * * *